(12) United States Patent
Zicker et al.

(10) Patent No.: US 6,914,071 B2
(45) Date of Patent: Jul. 5, 2005

(54) ANTIOXIDANT CONTAINING COMPOSITION AND METHOD

(75) Inventors: Steven Curtis Zicker, Lawrence, KS (US); Karen J. Wedekind, Meriden, KS (US)

(73) Assignee: Colgate-Palmolive Company, Piscataway, NJ (US)

( * ) Notice: Subject to any disclaimer, the term of this patent is extended or adjusted under 35 U.S.C. 154(b) by 0 days.

(21) Appl. No.: 09/978,132

(22) Filed: Oct. 16, 2001

(65) Prior Publication Data

US 2002/0119182 A1 Aug. 29, 2002

Related U.S. Application Data

(63) Continuation-in-part of application No. 09/922,660, filed on Aug. 6, 2001, now abandoned.
(60) Provisional application No. 60/244,504, filed on Oct. 31, 2000, and provisional application No. 60/253,448, filed on Nov. 28, 2000.

(51) Int. Cl.$^7$ .................. A61K 31/205; A61K 31/355; A61K 31/375; A61K 31/385
(52) U.S. Cl. ............... 514/440; 514/458; 514/474; 514/556
(58) Field of Search ................. 514/440, 458, 514/474, 556

(56) References Cited

U.S. PATENT DOCUMENTS

| 5,883,083 | A | | 3/1999 | Harless ................ 514/78 |
| 5,916,912 | A | | 6/1999 | Ames et al. ........... 514/440 |
| 6,080,788 | A | * | 6/2000 | Sole et al. ............ 514/561 |
| 6,335,361 | B1 | | 1/2002 | Hamilton ............. 514/440 |

FOREIGN PATENT DOCUMENTS

| CA | 2285490 | | 4/2001 |
| WO | 94/02036 | * | 2/1994 |
| WO | 0044375 | | 8/2000 |
| WO | WO0044375 | | 8/2000 |
| WO | 0158271 | | 8/2001 |
| ZA | 0965149 | | 6/1996 |

OTHER PUBLICATIONS

Crayhon, R., Total Health, Apr./May 1998, 20/2 (27–35).*
Emmons, Becky, South Bend Tribune, South Bend, Indiana (Aug. 25, 1999).*
CA 113:71127 (1990).*
CA 120: 45784 (1993).*
Branam, J. Edward "Dietary Management of Geriatric Dogs and Cats"; Veterinary Technician; vol. 8, No. 10 (1987) pp. 501–503.
Oxidative stress and Alzheimer disease; Yves Christen; American Journal Clinical Nutrition, 2000; 71 (suppl); pp. 621S–629S.

The Free Radical Theory of Aging Matures; Beckman et al; Physiol. Rev. 78; pp. 547–581; 1998.
Regular exercise improves cognitive function and decreases oxidative damage in rat brain; Radak et al; Neurochemistry International 38 (2001); pp. 17–23.
Increased Nuclear DNA Oxidation in the Brain in Alzheimer's Disease; Gabbita et al; Journal of Neurochemistry; Lippincott–Raven Publishers; pp. 2034–2040.
Four–Hydroxynonenal, a Product of Lipid Peroxidation, is Increased in the Brain in Alzheimer's Disease; Markesbery et al; Neurobiology of Aging; vol. 19, No. 1, 1998; pp. 33–36.
Elevated 4–Hydroxynonenal in Ventricular Fluid in Alzheimer's Disease; Lovell et al; Neurobiology of Aging; vol. 18, No. 5, 1999; pp. 457–461.
Increased DNA Oxidation and Decreased Levels of Repair Products in Alzheimer's Disease Ventricular CSF; Lovell, et al; Journal of Neurochemistry; 1999; pp. 771–776.
4–Hydroxynonenal Increases Neuronal Susceptibility to Oxidative Stress; Keller et al; Journal of Neuroscience Research; vol. 58, 1999; pp. 823–830.
Oxidationof Cytosolic Proteins and Expression of Creatine Kinase BB in Frontal Lobe in Different Neurodegenerative Disorders; Aksenova et al; Dement.Geriatr. Cogn. Disord.; vol. 10, 1999; pp. 158–165.
Stress, Aging, and Brain Oxidative Damage; Liu et al; Neurochemical Research; vol. 24, No. 11, 1999; pp. 1479–1497.
Increased F2–isoprostanes in Alzheimer's Disease: Evidence for Enhanced Lipid Peroxidation in vivo; Practico et al; The FASEB Journal; vol. 12, Dec. 1998; pp. 1777–1782.
4–Hydroxynonenal, a Product of Lipid Peroxidation, Damages Cholinergic Neurons and Impairs Visuospatial Memory in Rats; Bruce–Keller et al; Journal of Neuropathology and Experimental Neurology; vol. 57, No. 3, Mar. 1998; pp. 257–267.
A healthy body, a healthy mind: long–term impact of diet on mood and cognitive funciton; Peter J. Rogers; Proceedings of the Nutrition Society; vol. 60, 2001; pp. 135–143.
Vitamin E. Status and Neurodegenerative Disease; Michael J. Fryer; Nutritional Neuroscience; pp. 327–350.
Diet and Dementia, is there a Link? A Systematic Review; E. Ernst; Nutritional Neuroscience; vol. 2, 1999; pp. 1–6.
Vitamin E and Alzheimer disease: the basis for additional clinical trials; Michael Grundman; American Journal of Clinical Nutrition; vol. 71 (suppl), 2000; pp. 630S–636S.
Alzheimer disease: protective factors; Nourhashemi et al; American Journal of Clinical Nutrition; vol. 71 (suppl), 2000; pp. 643S–649S.

(Continued)

Primary Examiner—Phyllis G. Spivack
(74) Attorney, Agent, or Firm—Harness, Dickey & Pierce, P.L.C.

(57) ABSTRACT

A companion pet diet meeting ordinary nutritional requirements of the pet and further comprising a sufficient amount of an antioxidant or mixture thereof to inhibit the onset of deterioration of the mental capacity of said companion pet in its aged years.

11 Claims, No Drawings

OTHER PUBLICATIONS

Chronic antioxidant treatment improves the cognitive performance of aged rats; Socci et al; Brain Research, 693; 1995; pp. 88–94.

Association of Antioxidants with Memory in a Multiethnic Elderly Sample Using the Third National Health and Nutrition Examination Survey; Perkins et al; American Journal Epidemiol; vol. 150, No. 1, 1999; pp. 37–44.

Age–related changes in LTP and antioxidant defenses are reversed by an a–lipoic acid enriched diet; McGahon et al; Neurobiology of Aging; vol. 20, 1999; pp. 655–664.

Nutrients, age and cognitive function; Riedel et al; Mental Care; 1998; pp. 579–585.

Neurobehavioral aspects of antioxidants in aging; Cantuti–Castelvetri et al; Neuroscience; vol. 18, 2000; pp. 367–381.

Poster; Landmark Discrimination Learning In Aged Dogs Is Improved By Treatment with An Antioxidant Enriched Diet; Milgram et al; Nov. 5, 2000.

"Landmark Discrimination Learning In Aged Dogs is Improved by Treatment with An Antioxidant Enriched Diet," Milgram et al; Oct. 2000 prior to Oct. 31, 2000, citation on Internet Website.

"Oxidants, Antioxidants, and the Degenerative Diseases of Aging", Ames et al; Proc. National Acad. Science, USA; vol. 90; Sep. 1993; pp. 7915–7922.

"Effect of Vitamin and Trace–Element Supplementation on Cognitive Function in Elderly Subjects", Chandra et al; Nutrition, 17; 2001; pp. 709–712.

"The Canine as an Animal Model of Human Aging and Dementia", Cummings et al; Neurobiology of Aging; vol. 17; No. 2; 1996; pp. 259–268.

"Oxidative Alterations in Alzheimer's Disease", Markesbery et al; Brain Pathology, 9; 1999; pp. 133–146.

"Nutritional Antioxidants as Antidegenerative Agents", Ruvo et al; International Journal of Developmental Neuroscience; 2000; pp. 359–366, vol. 18.

Antioxidant–rich diets, improve cerebellar physiology and motor learning in aged rats; Bickford et al; Brain Research; vol. 866, 2000; pp. 211–217.

A controlled trial of selegiline, alpha–tocopherol, or both as treatment for Alzheimer's disease; Sano et al; The New England Journal of Medicine; vol. 336, 1997; pp. 1216–1222.

Alpha–Lipoic Acid as a Biological Antioxidant; Packer et al; Free Radical Biology and Medicine; vol. 19, No. 2, 1995; pp. 227–250.

Oxidative stress protection and vulnerability in aging: putative nutritional implications for intervention, Joseph et al; Mechanisms of Aging and Development; vol. 116, 2000; pp. 141–153.

Caprioli, A. et al. (1990): *Age–Dependent Deficits in Radial Maze Performance in the Rat: Effect of Chronic Treatment With Acetyl–L–Carnitine*; Prog. Neuro–Psychopharmacol. & Biol. Psychiat.14, 359–369 (Chem. Abs. 113:71127).

Crayhon, R.;Total Health, 20/2, pp 27–35, Apr./May (1998).

Emmons, B (1999): *Antioxidants to the rescue*; South Bend Tribune, South Bend, IN, Aug. 25, 1999.

Milgram, N.W. et al. (2000): *Landmark Discrimination Learning in Aged Dogs is Improved By Treatment With An Antioxidant Enriched Diet*, http://sfn.scholarone.com/itin2000/main.html?new_page_id=76&abstract_id=4237&is_tech=0.

Stoll, S. et al. (1993): *The Potent Free Radical Scaventer α–Lipoic Acid Improves Memory in Aged Mice: Putative Relationship to NMDA Receptor Deficits*; Pharmacology Biochemistry and Behavior 46, 799–805 (Chem. Abs. 120:45784).

* cited by examiner

# ANTIOXIDANT CONTAINING COMPOSITION AND METHOD

RELATED APPLICATION

This application is a continuation-in-part of U.S. Ser. No. 09/922,660 filed Aug. 6, 2001 now abandoned which claims benefit of Provisional Application No. 60/244,504 filed Oct. 31, 2000 and Provisional Application No. 60/253,448 filed Nov. 28, 2000.

BACKGROUND OF THE INVENTION

Companion animals such as dogs and cats seem to suffer from aging problems. Some of these are manifested in commonplace sayings. One of these is "You can't teach an old dog new tricks". This saying arises from the observation that as dogs age, their mental capacity seems to diminish as well as physical abilities. Mental activities associated with thinking learning and memory seem to be lessened (Cummings B J, Head E, Ruehl W, Milgram N W, Cotman C W 1996: The canine as an animal model of aging and dementia; Neurobiology of aging 17:259–268). Additionally, behavioral change can be manifested in the aging animals in association with the changing mental capacity. Many causes have been assigned to this lessening of capacity.

These losses in capacity are generally observed in aged canines and felines. Dogs of seven years or older and felines of seven years or older are considered aged and can experience this problem.

The presence of significant levels of at least one antioxidant in the diet of an adult companion pet or fed to a pet outside his diet can inhibit the onset of deterioration of the mental capacity of the aged companion pet and/or maintain the mental capacity of the adult companion pet further into the aged years.

SUMMARY OF THE INVENTION

In accordance with the invention, there is a companion pet diet meeting ordinary nutritional requirements of an adult pet and further comprising a sufficient amount of an antioxidant or mixture thereof to inhibit the onset of deterioration of the mental capacity of said companion pet in its aged years.

A further aspect of the invention is a method for inhibiting the deterioration of the mental capacity of an aged companion pet, which comprises feeding said pet in his adult years an antioxidant or mixture thereof at sufficient levels to accomplish this inhibition.

In further accordance with the invention is a companion adult pet diet meeting ordinary nutritional requirements of an adult companion pet and further comprising an antioxidant selected from the group consisting of Vitamin E, vitamin C, alpha-lipoic acid, l-carnitine and any mixtures thereof in quantities sufficient to inhibit the deterioration of the mental capacity of said pet in its aged years.

A still further aspect of the invention is a method for increasing the mental capacity of an aged companion pet, which comprises feeding the pet in its adult years an amount of an antioxidant or mixture thereof sufficient to increase the mental capacity.

Another aspect of the invention is a method for increasing the mental capacity of an adult companion pet which comprises feeding the pet an amount of an antioxidant or mixture thereof sufficient to increase the mental capacity of said pet.

In all of these methods, it is desirable to administer the antioxidant or mixture thereof in the diet of the animal.

DETAILED DESCRIPTION OF THE INVENTION

The diet fed to the adult companion pet, for example canine and feline is the standard normal diet fed to an animal of that age. Below is a typical diet for a canine of 1 to 6 years of age.

TABLE 1

| Component | Target |
|---|---|
| Protein (% of dry matter) | 23 |
| Fat (% of dry matter) | 15 |
| Phosphorous (% of dry matter) | 0.6 |
| Sodium (% of dry matter) | 0.3 |

Adding significant quantities of an antioxidant or mixture thereof to the companion adult pet diet can bring about delay of the onset of demonstrative changes in the behavior, particularly the deterioration of mental capacity, as specifically shown by problem-solving capacity, in an aged pet. The term, adult, is intended to mean, in general, a canine of at least 1 to 6 years and a feline of at least 1 to 6 years. An aged dog or cat is 7 years and above.

The loss of mental capacity for canines and felines has been observed for a number of years. This loss of mental capacity is manifested in numerous ways. For a canine, for example, it can be manifested as disorientation, house soiling, altered sleep-wake patterns, decreased or altered interaction with humans and other pets, and inability to learn and concentrate. These conditions can be manifested in felines as well. Alzheimer's, as exhibited in man, is not found in canines and felines.

Many theories have been advanced for this loss in mental capacity. To date, the inventors are unaware of any dietary course of action, which inhibits this loss of mental capacity or can actually bring about a positive change in mental capacity as measured by an objective parameter in dogs and cats.

The inventors have succeeded in accomplishing delaying the onset of this deterioration. By using the diet of their invention in adult companion pets it can be shown that aged pets mental capacity can be maintained for a longer period of time. Essentially the deterioration of mental capacity can be stopped or delayed. Memory and learning ability can be improved. Overall mental alertness can be enhanced. Age related cognitive decline could be slowed. With respect to Cognitive Dysfunction Syndrome its progress can be slowed in aged dogs and clinical signs associated with this Syndrome can be controlled. Prophylaxis where appropriate and pets in need of these components are the target group.

The component in the diet, which accomplishes this is an antioxidant or mixture thereof. An antioxidant is a material that quenches a free radical. Examples of such materials include foods such as Ginkgo Biloba, citrus pulp, grape pomace, tomato pomace, carrot and spinach, all preferably dried as well as various other materials such as beta-carotene, selenium, coenzyme Q10 (ubiquinone), lutein, tocotrienols, soy isoflavones, S-adenosylmethionine, glutathione, taurine, N-acetylcysteine, Vitamin E, Vitamin C, alpha-lipoic acid, l-carnitine and the like. Vitamin E can be administered as a tocopherol or a mixture of tocopherols and various derivatives thereof such as esters like vitamin E acetate, succinate, palmitate, and the like. The alpha form is preferable but beta, gamma and delta forms can be included. The d form is preferable but racemic mixtures are acceptable. The forms and derivatives will function in a Vitamin E like activity after ingestion by the pet. Vitamin C can be administered in this diet as ascorbic acid and its various derivatives thereof such as calcium phosphate salts, cholesteryl salt, 2-monophosphate, and the like which will function in a vitamin C like activity after ingesting by the pet. They can be in any form such as liquid, semisolid, solid and heat stable form. Alpha-lipoic acid can be administered into the diet as alpha lipoic acid or as a lipoate derivative as in U.S. Pat. No. 5,621,117, racemic mixtures, salts, esters or amides thereof. L-carnitine can be administered in the diet and various derivatives of carnitine such as the salts such as the hydrochloride, fumarate and succinates, as well as acetylated carnitine, and the like can be used.

The quantities administered in the diet, all as wt % (dry matter basis) of the diet, are calculated as the active material, per se, that is measured as free material. The maximum amounts employed should not bring about toxicity. At least about 100 ppm or at least about 150 ppm of Vitamin E can be used. A preferred range of about 500 to about 1,000 ppm can be employed. Although not necessary a maximum of about 2000 ppm or about 1500 ppm is generally not exceeded. With respect to Vitamin C at least about 50 ppm is used, desirably at least about 75 ppm and more desirably at least about 100 ppm. A nontoxic maximum can be employed. The quantity of alpha-lipoic acid can vary from at least about 25, desirably at least about 50 ppm, more desirably about 100 ppm. Maximum quantities can vary from about 100 ppm to 600 ppm or to an amount which remains non toxic to the pet. A preferred range is from about 100 ppm to about 200 ppm. For l-carnitine about 50 ppm, desirably about 200 ppm, more desirably about 300 ppm for canines are a useful minimum. For felines, slightly higher minimums of l-carnitine can be employed such as about 100 ppm, 200 ppm, and 500 ppm. A nontoxic maximum quantity can be employed, for example, less than about 5,000 ppm. For canines, lower quantities can be employed, for example, less than about 5,000 ppm. For canines a preferred range is about 200 ppm to about 400 ppm. For felines a preferred range is about 400 ppm to about 600 ppm.

Beta-carotene at about 1–15 ppm can be employed.
Selenium at about 0.1 up to about 5 ppm can be employed.
Lutein at least about 5 ppm can be employed.
Tocotrienols at least about 25 ppm can be employed.
Coenzyme Q10 at least about 25 ppm can be employed.
S-adenosylmethionine at least about 50 ppm can be employed.
Taurine at least about 1000 ppm can be employed.
Soy isoflavones at least about 25 ppm can be used.
N-acetylcysteine at least about 50 ppm can be used.
Glutathione at least about 50 ppm can be used.
Gingko Biloba at least 50 ppm of extract can be used.

The following are raw ingredients that are high in ORAC (Oxygen radical absorbing capacity) content. When added to the diet as 1% inclusions (for a total of 5% substitution for a low ORAC ingredient such as corn) they increased the ORAC content of the overall diet and increased the ORAC content of the plasma of the animals which ate the diet containing these components. Preferably, any ingredient with an ORAC content >25 umole of Trolox equivalents per gram of dry matter could be used if added at 1% combination with four other 1% ingredients for a total of 5% addition to the diet.

Spinach pomace
Tomato pomace
Citrus Pulp
Grape Pomace
Carrot granules
Broccoli
Green tea
Ginkgo Biloba
Corn gluten meal

EXAMPLE 1

Seventeen adult beagle dogs 2–4 years of age (control n=8, antioxidant-enriched n=9) were randomly placed into a control or enriched diet group. The control diet contained 59 ppm Vitamin E and <32 ppm Vitamin C. The test diet had 900 ppm Vitamin E and 121 ppm Vitamin C, 260 ppm l-carnitine and 135 ppm alpha lipoic acid. Approximately 1 month after starting the diet, the first problem-solving task given to dogs was a landmark discrimination learning task, which is a test of spatial attention (Milgram et al., 1999 Milgram, N. W., Adams, B., Callahan, H., Head, E., Mackay, B., Thirlwell, C., & Cotman (1999), C. W. Landmark Discrimination Learning in the Dog. Learning & Memory, 6:54–61).

Landmark discrimination learning requires subjects to select a particular object based on proximity to an object. The initial learning, however, is based on the dogs' ability to learn an object discrimination task. We have previously found that the effects of age on discrimination learning depends on task difficulty.

The adult dogs on the enriched diet made fewer errors than the adult dogs on the control food when learning the landmark 0 test (control mean=31.1, enriched mean=15.1). The adult dogs proceeded on to landmark 1 and 2 testing, where the landmark is moved further away from the positive well. Adult dogs on enriched diet learned landmark 0–2 with less errors than those on the control (number of mean errors landmark 0+1+2 control=132.9; number of mean errors of dogs on enriched diet landmark 0+1+2=87.1).

EXAMPLE 2

30 adult, random source, dogs were utilized for this study. Dogs were at least 10 months of age, not pregnant, not lactating and of reasonable body weight prior to start of test. Animals were randomized into 5 groups for dietary treatment with 3 males and 3 females per each group.

All dogs were fed a control food (0 ppm dl-alpha-lipoic acid added) that met or exceeded all recommendations for nutrients as proposed by the American Association of Feed Control Officials (AAFCO 2000) during a 2 week prefeeding period (Table 1). Following the prefeeding period dogs were randomized into 5 treatment groups with one of the following dl-alpha lipoic acid target-inclusions (dry matter basis): 0 ppm, 150 ppm, 1500 ppm, 3000 ppm, 4500 ppm. In all diets, control and alpha lipoic acid, Vitamin E was added and was present at a level of 600–1000 International Units and Vitamin C was added at levels of 100–200 ppm.

Test foods were the sole source of nutrients except for water. Fresh water was provided ad libitum. After dogs were selected and initial body weights taken, a food dose was calculated for each dog based on the expected ME of the food. Initial food dose calculations were based on the maintenance energy requirement (MER) for the dog modified by a factor to account for normal activity as calculated by the following formula:

$$MER(kcal/day)=1.6 \times RER(\text{Resting Energy Requirement})$$

Where: $RER(kcal/day)=70 \times \text{body weight (kg)}0.75$

Dogs were weighed weekly and had food doses adjusted as needed in order to feed enough food to maintain their optimal body weight. Optimal body weight was determined to be 3 on a 5 point scale. If a dog did not maintain body weight within −10% of initial body weight, after adjustment of food dose, it was removed from the study. All measures of body weight and food intake were recorded.

Samples were ground and 0.100±0.001 g of sample was extracted twice into 5.0 mL phosphate buffer (10 mM $Na_2HPO_4$, 2 mM ethylenediaminetetraacetatic acid (EDTA), 0.9% NaCl, pH 7.4)[4]. 250 $\mu$L of extract was placed into a 5 mL glass centrifuge tube with a Teflon lined cap. 15 $\mu$L EDTA solution (100 mM EDTA, adjusted to pH 7.8 with ~1M NaOH) and 50 $\mu$L freshly prepared 5 mM dithioerythritol (DTE) were added. The solutions were vortexed and incubated at room temperature for 5 minutes. Then 10 $\mu$L of 1M $H_3PO_4$ and 2.0 mL diethyl ether were added. The tubes were capped, vortexed, and centrifuged at 1500×g for 3 minutes at room temperature. The ether layer was transferred to a separate 5 mL glass centrifuge tube, while the aqueous layer was extracted twice more with 1.5 mL ether. All extractions from the same sample were combined. The extracts are then dried in a nitrogen evaporator in a water bath at room temperature. At this point, the samples were capped and frozen overnight.

The dried extracts were then thawed and reconstituted with 70 $\mu$L SDS/EDTA solution (0.11% sodium dodecyl sulfate (SDS), 15 mM EDTA, 0.9% NaCl) and 5 $\mu$L freshly prepared 1 mM DTE. 50 $\mu$L of freshly prepared $NaBH_4$ was then added to each tube. The tubes were vortexed and incubated at room temperature for 10 minutes. After 10 minutes, the samples were frozen at −70° C. Before the solutions were thawed, 20 $\mu$L 2M HCl was added. After the solutions were thawed, 800 $\mu$L 100 mM $NH_4HCO_3$ was added. The solutions are vortexed and 5 $\mu$L of 100 mM momobromobimane in acetonitrile solution (mBBr) was added. The solutions were then incubated in the dark for 90 minutes at room temperature.

Excess mBBr and the DTE derivative were removed from the samples after incubation by extraction with 1.5 mL dichloromethane. The aqueous layer was placed on the HPLC. The lipoic acid was separated using a mobile phase that consisted of 30% acetonitrile, 1% acetic acid, adjusted to pH 3.95 with ~2M $NH_4OH$ and was pumped at a flow rate of 1.0 mL/min with an isocratic elution for 15 minutes per injection. This preparation assumes that the density of the extruded food is equal to 1 g/mL.

Blood was collected aseptically for complete blood count, and blood biochemistry analysis 2 weeks prior to start and again at 0, 28, 56, 84, 112, 140 and 168 days of the study. In addition, 15 ml of whole blood was collected for isolation of lymphocytes at day 0, 28 and 84 of the dietary intervention.

Heparainzed whole blood was layered onto a 50 ml Accuspin conical centrifuge tube (Sigma Chemical) and an equal volume of Phosphate buffered saline (PBS) was added. Samples were centrifuged at at 700 g for 30 minutes without brake. The monocyte layer was harvested, transferred to a 15 ml conical centrifuge tube, resuspended in 1–3 ml of PB, and centrifuged as before (First wash). A second wash was performed as the first wash. Finally, cells were harvested and suspended in perchloric acid (10% w/v) and frozen at −70C until analysis.

Samples were transferred from −70° C. freezer into a cooler with dry ice in it. Vials were centrifuged at 12,000 rpm for 5 minutes in a refrigerated centrifuge. An aliquot of supernatant for glutathione (GSH) analysis was transferred to a conical test tube.

Derivatization of the acid soluble extracts was by the method of Reed and coworkers (Fariss et al) as modified by Jones (Jones et al)

Briefly, 150 $\mu$l extract or external standards were added into a 1.5 ml eppendorf tube followed by addition of 20 $\mu$γ-glu-glu internal standard and 50 $\mu$l IAA added followed by mixing. The solution was adjusted to pH~10 (purple color) by using $KOH-KHCO_3$ working solution. Solutions were incubated 1 hr. under room temperature in the dark. Sanger's reagent was added at the same volume as of the total volume and the solution was incubated overnight (20 hrs) in the dark at room temperature.

After incubation, the solution was centrifuged at 12000 rpm for 5 minutes with the supernatant transferred into another 1.5 ml eppendorf tube. 200 $\mu$l supernatant was added into an amber autovial which had a 300 $\mu$l inlet, fix the top with a crimper for HPLC analysis.

Solvents and separation conditions were as described (Fariss, Jones). Levels of GSH and GSSG were quantified relative to authentic standards. Gamma-glutamyl-glutamate was used as an internal standard to assess derivatization efficiency.

Comparison of values for clinical chemistry, hematology and body weights vs baseline were analyzed by way of paired t-test on SAS for windows with significance set at $P<0.05$. Means of values at each measured time point were separated by a one-way ANOVA with significance set at $P<0.05$. The difference in GSH:GSSG between day 84 and baseline were analyzed between groups by way of SAS for windows in a one-way ANOVA with significance set at $P<0.05$.

Results

Concentrations of lipoic acid (ppm) in food as determined over 7 successive assays (0, 28, 56, 84, 112, 140, 168 days) were within the range of expected assay sensitivity and production parameters typically encountered at our facility (Table 1).

The food intake data were unremarkable. Most animals in all groups ingested more food at 6 months, on average, than at the beginning of the study. Body weight data were unremarkable except that some weight loss occurred initially in the 4500 ppm inclusion group but that change appeared to reversed by 6 months time. Body condition scores did not appear to be affected by this minor loss of weight.

The routine physical examinations did not reveal any evidence of nutrition related abnormalities or dl-alpha-lipoic acid toxicity. All animals in the study population remained normal during the entire course of the study. Occasional vomiting was observed in several animals during the course of the study; however, a trend was not observed that would lead one to the conclusion that the vomiting may be attributable to lipoic acid. One animal, in the highest inclusion group, was dropped from the study at day 21 for weight loss and leukocytosis. The leukocytosis in this animal had not resolved by the end of the study and is suspected to be attributable to some other disease process.

When serum biochemistry values for days 28, 56, 84, 112, 140, and 168 were compared with the initial values for the same group of dogs, several statistical differences were noted, however, none of these were considered biologically significant because these values were within or very near the laboratory reference range and consistent trends over months were noted. Comparisons between the controls and the other treatment groups at each time period also revealed several statistical differences, however, none of these were considered biologically significant because these values were within or very near the clinical laboratory reference ranges and no trends were present.

When the hematology values for days 28, 56, 84, 112, 140 and 168 were compared with the initial values for the same group of dogs, several statistical differences were noted; however, none of these were considered biologically significant because these values were within or very near the laboratory reference range and not trends were present. Comparison between the controls and the other treatment groups at each time period revealed several statistical differences; however, none of these were considered biologically significant because these values were within or very near the clinical laboratory reference ranges and no trends were present.

GSH:GSSG ratio

The change in GSH:GSSG ratio over 84 days of feeding displayed a significant overall effect of diet (P=0.024) with all supplemented groups having an increase in the ratio (Table 2). ANOVA revealed a significant difference, compared to the basal food, for the lowest and highest inclusions, however, the largest numerical increase was in the lowest inclusion level. That is to say, the changes in the GSH:GSSG ratio for the highest and lowest inclusion were significantly different from the change observed over this same time period in the basal food. Ratios for 4 points could not be determined at day 84 as no GSSG was detectable in any of these samples (1 control, 3 treatment groups). As such, the values for supplemented groups may have displayed even higher ratios of GSH:GSSG if the assay had been sensitive enough to detect the low levels of GSSG at day 84.

TABLE 1

| Inclusion Rate (ppm) | Average | Standard Deviation | Percent Target |
|---|---|---|---|
| 0 | 24 | 17 | NA |
| 150 | 151 | 13 | 101 |
| 1500 | 1471 | 113 | 98 |
| 3000 | 2869 | 250 | 96 |
| 4500 | 4176 | 642 | 93 |

TABLE 2

Change in mean ratio of GSH:GSSG from day 0 to day 84 in dogs consuming dl-alpha lipoic acid in an extruded food.

| Inclusion | Difference in GSH: GSSG ratio-d 0 to d 84 compared to baseline food | N | P value |
|---|---|---|---|
| 0 ppm | −9.2 ± 26 | 5* | NA |
| 150 ppm | 70 ± 20 | 6 | .003 |
| 1500 ppm | 24 ± 7 | 6 | .16 |
| 3000 ppm | 10 ± 4 | 4* | .46 |
| 4500 ppm | 50 ± 36 | 4* | .03 |

*1 dog in the control and 4500 ppm group had no detectable GSSG at day 84 while 2 dogs in the 3000 ppm group had no detectable GSSG at day 84.

Further observations with respect to alpha lipoic acid are applicable. Chronic feeding of alpha lipoic acid in diet is safe and effective. It improves the reduced glutathione (GSH) to oxidized glutathione (GSSG) ratio. The chronic administration of alpha lipoic acid in the diet can be for periods of one, two, three, four, five, or six months minimum up through a period of one, two, three, four, five years or even more including the lifetime of the animal. The alpha lipoic acid functions without any special protection in the diet such as encapsulation and need not be present in the diet in a unit dosage form such as those used in pharmaceuticals for example, tablet, pill, capsule and the like. The lipoic acid is provided in the diet in a minimum of about 25, 50, 75, or 100 ppm of diet. The uppermost range is just below its toxic level, all the way down to about 400, 300, or 200 ppm of diet. Generally, one does not go beyond about 6 or 7 mg/kg body weight of animal per day, more generally not above about 5. The alpha lipoic acid improves antioxidant defense capabilities as well as improves the animal's ability to resist oxidative damage. All this is done with the proper quantities of other antioxidants present such as Vitamin E and Vitamin C. This demonstrates that the action of alpha lipoic acid is beyond that of Vitamin C and/or Vitamin E.

What is claimed is:

1. A method for inhibiting the onset of deterioration of the mental capacity of a canine or feline companion pet of 7 years or older, the method comprising feeding said pet when it is 1 to 6 years old a diet that comprises a sufficient amount of an antioxidant or mixture of antioxidants to accomplish this inhibition.

2. The method of claim 1 wherein the pet is a canine.

3. The method of claim 1 wherein the pet is a feline.

4. The method of claim 1 wherein Vitamin E is fed to the pet in an amount of at least about 100 ppm of the diet.

5. The method of claim 4 wherein an antioxidant selected from the group consisting of Vitamin C, L-carnitine, alpha-lipoic acid and mixtures thereof is fed to the pet.

6. The method of claim 1 wherein an antioxidant selected from the group consisting of Vitamin C, L-carnitine, alpha-lipoic acid and mixtures thereof is fed to the pet.

7. The method of claim 6 wherein Vitamin C is fed to the pet in an amount of at least about 50 ppm of the diet.

8. The method of claim 6 wherein alpha-lipoic acid is fed to the pet in an amount of at least about 25 ppm of the diet.

9. The method of claim 6 wherein L-carnitine is fed to the pet in an amount of at least about 50 ppm of the diet.

10. A method for improving a canine or feline companion pet's ability when 7 years or older to resist oxidative damage, the method comprising feeding said pet when it is 1 to 6 years old a diet meeting nutritional requirement, said diet having at least about 25 ppm alpha-lipoic acid and said diet being fed for at least one month.

11. A method for inhibiting the loss of learning ability of a canine or feline companion pet of 7 years or older, the method comprising feeding the pet when it is 1 to 6 years old an antioxidant or mixture of antioxidants at levels sufficient to accomplish said inhibiting, said antioxidant being selected from the group consisting of Vitamin E, Vitamin C, alpha-lipoic acid, L-carnitine and mixtures thereof.

* * * * *